United States Patent
Pan et al.

(10) Patent No.: US 10,857,083 B2
(45) Date of Patent: Dec. 8, 2020

(54) AMINO ACID CARBAMATE COMPLEXES

(71) Applicant: Colgate-Palmolive Company, New York, NY (US)

(72) Inventors: Long Pan, Somerset, NJ (US); Donghui Wu, Bridgewater, NJ (US); Ravi Subramanyam, Belle Mead, NJ (US); Hongwei Shen, Holmdel, NJ (US); Chi-Yuan Cheng, Hillsborough, NJ (US); Tatiana Brinzari, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/216,533

(22) Filed: Dec. 11, 2018

(65) Prior Publication Data

US 2019/0183765 A1 Jun. 20, 2019

Related U.S. Application Data

(60) Provisional application No. 62/607,376, filed on Dec. 19, 2017.

(51) Int. Cl.

| | |
|---|---|
| *A61K 8/44* | (2006.01) |
| *A61Q 11/00* | (2006.01) |
| *C07C 271/06* | (2006.01) |
| *C07C 279/14* | (2006.01) |
| *C07C 269/04* | (2006.01) |
| *A61K 31/4172* | (2006.01) |
| *A61K 8/21* | (2006.01) |
| *A61K 33/16* | (2006.01) |
| *A61K 31/198* | (2006.01) |
| *A61K 8/49* | (2006.01) |
| *A61K 8/19* | (2006.01) |

(52) U.S. Cl.
CPC ............. *A61K 8/44* (2013.01); *A61K 8/19* (2013.01); *A61K 8/21* (2013.01); *A61K 8/442* (2013.01); *A61K 8/445* (2013.01); *A61K 8/447* (2013.01); *A61K 8/492* (2013.01); *A61K 8/4946* (2013.01); *A61K 31/198* (2013.01); *A61K 31/4172* (2013.01); *A61K 33/16* (2013.01); *A61Q 11/00* (2013.01); *C07C 269/04* (2013.01); *C07C 271/06* (2013.01); *C07C 279/14* (2013.01); *A61K 2800/58* (2013.01)

(58) Field of Classification Search
None
See application file for complete search history.

(56) References Cited

U.S. PATENT DOCUMENTS

| | | |
|---|---|---|
| 3,538,230 A | 11/1970 | Pader et al. |
| 3,862,307 A | 1/1975 | Di Giulio |
| 3,937,807 A | 2/1976 | Haefele |
| 3,959,458 A | 5/1976 | Agricola et al. |
| 4,051,234 A | 9/1977 | Gieske et al. |
| 4,340,583 A | 7/1982 | Wason |
| 4,842,847 A | 6/1989 | Amjad |
| 4,866,161 A | 9/1989 | Sikes et al. |
| 4,937,083 A * | 6/1990 | Itagaki ............... A23K 40/35 426/302 |
| 5,004,597 A | 4/1991 | Majeti et al. |
| 5,188,821 A | 2/1993 | Gaffar et al. |
| 5,192,531 A | 3/1993 | Gaffar et al. |
| 8,399,704 B2 | 3/2013 | Kohli et al. |
| 9,029,598 B2 | 5/2015 | Garcia et al. |
| 2009/0202450 A1* | 8/2009 | Prencipe ............ A61Q 11/00 424/50 |

OTHER PUBLICATIONS

Pronamel commercial product obtained from website: https://www.pronamel.us/tooth-erosion/how-to-prevent-acid-erosion/?gclid=CjwKCAiA27LvBRBOEiwAPc8XWQuAVBzhTB9ih9LpZUYwsJgULsBhfA8FlgPb5vgaEX910HBwxPNTrRoCwFMQAvD_BwE&gclsrc=aw.ds, 2014. (Year: 2014).*

International Search Report and the Written Opinion of the International Searching Authority issued in international application PCT/US2018/064964 (dated Jun. 27, 2019).

* cited by examiner

*Primary Examiner* — Kyung S Chang

(57) ABSTRACT

Disclosed herein are amino acid carbamate complexes, methods of synthesis thereof, oral care compositions comprising the same, and methods of making and using thereof.

19 Claims, No Drawings

AMINO ACID CARBAMATE COMPLEXES

CROSS-REFERENCE TO RELATED APPLICATIONS

This application claims priority to and the benefit of U.S. Provisional Application No. 62/607,376, filed on Dec. 19, 2017, the contents of which are hereby incorporated by reference in its entirety.

FIELD

The present invention pertains to new complexes of amino acid carbamates, including the newly identified arginine/arginine carbamate complex having the formula $[(NH_2)_2-C-NH-(CH_2)_3-CH-(NH_3)-CO_2]^+$ $[(NH_2)_2-C-NH-(CH_2)_3CH(NH-CO_2)-CO_2]^-$, methods of synthesis of such complexes, and compositions comprising such complexes, as well as to concentrated solutions of amino acids, and methods of manufacture thereof and compositions comprising thereof.

BACKGROUND

Amino acids, such as lysine and arginine, as well as their salts and complexes, have been used in the past in oral care compositions because of their many known benefits. These benefits include, for example, the promotion of arginolytic bacterial growth, the suppression of cariogenic bacterial growth, the elevation of oral pH, inhibition of acid-induced dental erosion, and relief from dentinal hypersensitivity. Nevertheless, there continues to be a need for novel arginine complexes having new and useful chemical and/or physical properties which improve upon existing arginine salts and complexes.

Amino acids have the general formula $H_2N-CH(R)-COOH$, wherein R is a substituent which may be acidic, basic or neutral. Amino acids can exist in neutral or zwitterionic forms (e.g., $H_3N^+-CH(R)-COO^-$). For example, arginine is a highly basic amino acid having the following chemical structure in its neutral and zwitterionic forms:

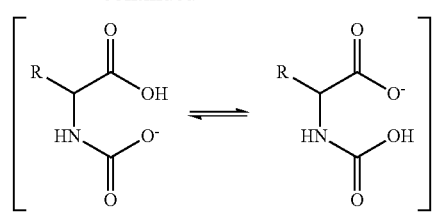

Amino acid carbamates are derivatives of amino acids in which the primary alpha-amino group is carboxylated to form a compound of generic formula $HO-(C=O)-NH-CH(R)-COOH$, referred to herein as "amino acid carbamate." An amino acid carbamate can be deprotonated by a suitable base to form a conjugate anion. The conjugate anion of a typical amino acid may take various equivalent tautomeric forms (which are interchangeable):

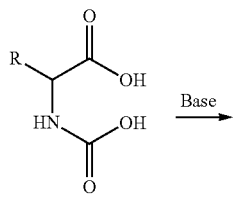

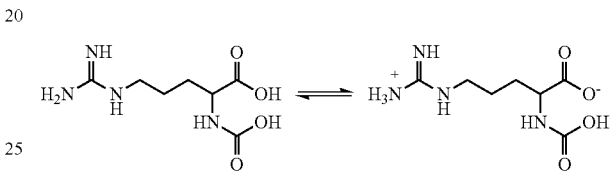

Like a neutral amino acid, the amino acid carbamate of a basic amino acid can exist in either neutral or zwitterionic form, because it retains both an acidic group and a basic group. Therefore, its conjugate anion can also exist in the form of either an anion or a zwitterionic anion. For example, arginine carbamate has the following structure, shown in the neutral and zwitterionic form:

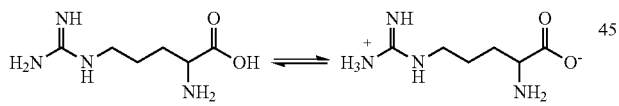

Arginine carbamate can be deprotonated by a base to form the following anionic species, which are tautomeric and interchangeable:

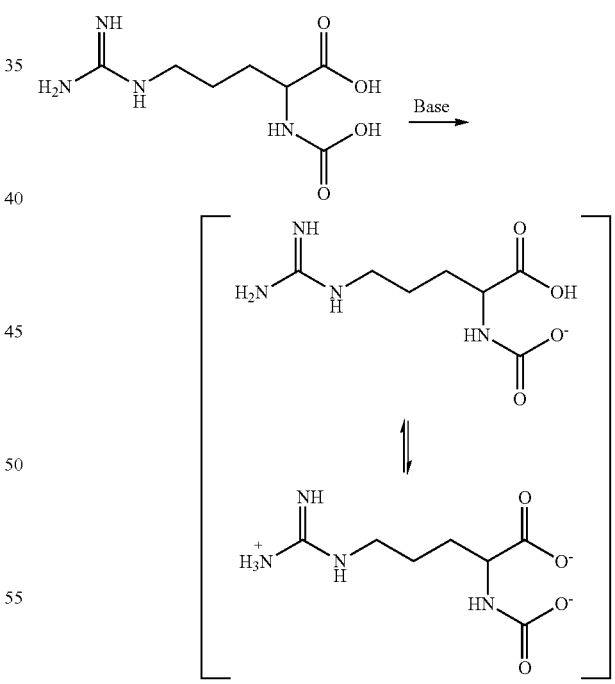

Inorganic salts of amino acids are known, including amino acid carbonates and carbamates. In the prior art, it has been known to synthesize the inorganic salts arginine bicarbonate ($Arg^+HCO_3^-$) and arginine carbonate ($Arg_2^{+2}CO_2^{-2}$) by bubbling carbon dioxide gas (or adding dry ice) into an aqueous solution of arginine, as shown below:

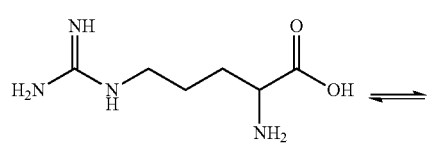

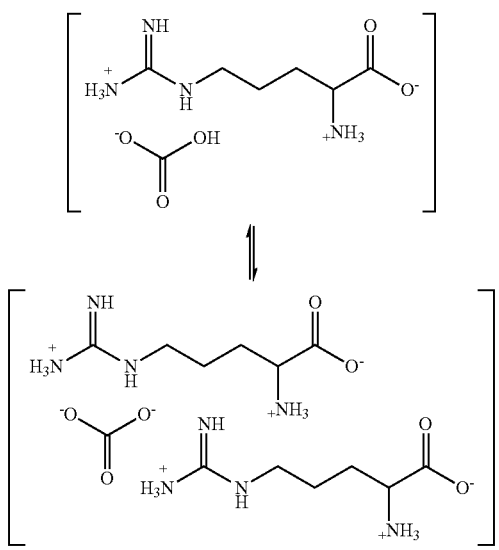

BRIEF SUMMARY

It has now been discovered that under certain conditions, arginine carbamate can react with metallic bases or with amino acids to form novel metal/amino acid carbamate and amino acid/amino acid carbamate complexes. These complexes have the general formula $M^+$[amino acid-carbamate]$^-$, wherein M is a metal ion or amino acid cation. It is understood that by indicating the negative charge outside of the bracketed amino acid it is intended that the negative charge can reside on any of the anionic oxygen atoms in the amino acid. Any amino acid is suitable, and therefore R can be the well-known "R-group" for any of the natural amino acids (e.g., the R group for glycine, arginine, lysine, histidine, alanine, valine, leucine, isoleucine, phenylalanine, tryptophan, glutamic acid, aspartic acid, glutamine, asparagine, serine, threonine, cysteine, methionine, proline, and tyrosine). M can be any monovalent cation, such as sodium, potassium or lithium. In particular embodiments, the present disclosure concerns complexes of an amino acid carbamate and a metal cation. For example:

In some embodiments, the present invention discloses that that under the proper conditions, the reaction of a free amino acid with carbon dioxide may yield an amino acid carbamate complex, rather than the amino acid carbonate salt of the prior art.

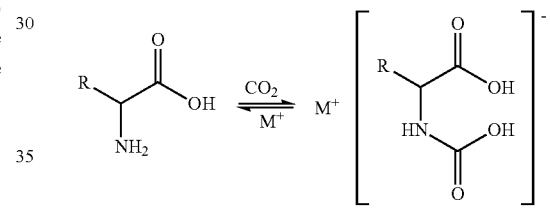

In particular embodiments, the present disclosure concerns complexes of an amino acid and its own carbamate. The group "R" is as noted above.

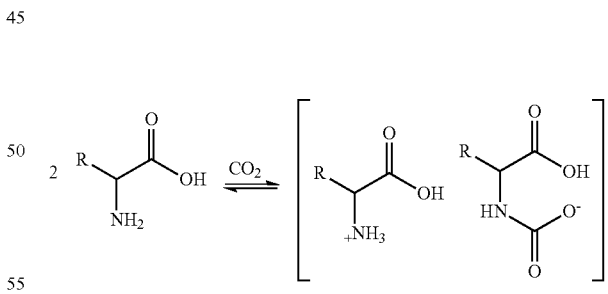

In particular embodiments, the present disclosure concerns complexes of arginine and arginine carbamate. The inventors have discovered that arginine free base will react with carbon dioxide in aqueous solution to form a previously unreported 1:1 arginine/arginine carbamate complex, [Arginine]$^+$[Arginine-Carbamate]$^-$, which may exist in the form of a dihydrate. In some embodiments, the reaction proceeds as shown below to form the arginine/arginine carbamate complex of the following formula:

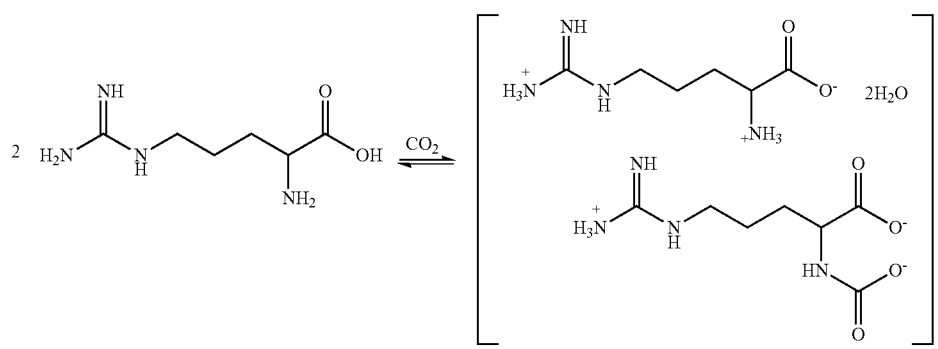

In some embodiments, the yield of the conversion of amino acid to amino acid carbamate is improved by the use of an additional inorganic base, in addition to the arginine free base. The additional base may be a hydroxide, oxide, carbonate, or bicarbonate base, e.g., an alkali metal base. For example, the base may be sodium hydroxide, potassium hydroxide, lithium hydroxide, sodium bicarbonate, potassium bicarbonate, lithium bicarbonate, sodium carbonate, potassium carbonate, lithium carbonate, sodium oxide, potassium oxide, or lithium oxide. The result of adding this base is that additional amino acid is converted into amino acid carbamate, and the result is a metal amino-acid carbamate complex (e.g., if NaOH is the base, the result is an Na/amino acid carbamate complex).

In some embodiments, the reaction takes place in aqueous solution at elevated temperature, for example, at least 50° C., or at least 60° C., at least 70° C., or at least 80° C. In some embodiments, the amino acid carbamate complex is isolated and/or purified.

The invention further provides an oral care composition, for example, a mouthwash, oral gel or dentifrice composition, that comprise the amino acid carbamate complex prepared according to the invention. The compositions may optionally further comprise a fluoride source and or an additional phosphate source. The compositions may be formulated in a suitable oral care formulation e.g., a conventional dentifrice, oral gel or mouthwash base, e.g., comprising one or more abrasives, surfactants, foaming agents, vitamins, polymers, enzymes, humectants, thickeners, antimicrobial agents, preservatives, flavorings, and/or colorants.

The invention further provides oral care methods of using the compositions of the invention to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying a composition of the invention to the teeth.

The invention further provides methods of making the compositions of the invention.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

In a first aspect, the invention provides, an amino acid carbamate complex of the formula $M^+$ [amino acid-carbamate]$^-$ which comprises an amino acid carbamate anion and a counterion M, wherein M is a metal cation or an amino acid cation (Complex 1).

In further embodiments of the first aspect, the invention provides:

1.1 Complex 1, wherein M is a metal ion selected from sodium, potassium and lithium.

1.2 Complex 1, wherein M is an amino acid (e.g. an amino acid cation).

1.3 Complex 1.2, wherein the amino acid M is the same as the amino acid of the amino acid carbamate.

1.4 Complex 1.2 or 1.3, wherein the amino acid M is selected from glycine, arginine, lysine, histidine, alanine, valine, leucine, isoleucine, phenylalanine, tryptophan, glutamic acid, aspartic acid, glutamine, asparagine, serine, threonine, cysteine, methionine, proline, and tyrosine.

1.5 Complex 1.2 or 1.3, wherein the amino acid is a basic amino acid.

1.6 Complex 1.2 or 1.3, wherein the amino acid is arginine, lysine or histidine.

1.7 Complex 1 or any of 1.1 et seq. wherein the amino acid carbamate is a carbamate of an amino acid selected from glycine, arginine, lysine, histidine, alanine, valine, leucine, isoleucine, phenylalanine, tryptophan, glutamic acid, aspartic acid, glutamine, asparagine, serine, threonine, cysteine, methionine, proline, and tyrosine.

1.8 Complex 1 or any of 1.1 et seq. wherein the amino acid carbamate is a carbamate of a basic amino acid.

1.9 Complex 1 or any of 1.1 et seq. wherein the amino acid carbamate is a carbamate of arginine, lysine or histidine.

1.10 Complex 1 or any of 1.1 et seq. wherein the complex has the formula [glycine]$^+$[glycine carbamate]$^-$.

1.11 Complex 1 or any of 1.1 et seq. wherein the complex has the formula [lysine]$^+$[lysine carbamate]$^-$.

1.12 Complex 1 or any of 1.1 et seq. wherein the complex has the formula [arginine]$^+$[arginine carbamate]$^-$.

1.13 Complex 1 or any of 1.1 et seq. wherein the complex has the formula Na$^+$[arginine carbamate]$^-$ or Na$^+$[lysine carbamate]$^-$ or Na$^+$[glycine carbamate]$^-$.

1.14 Complex 1 or any of 1.1 et seq. wherein the complex is an arginine/arginine carbamate complex of the formula:

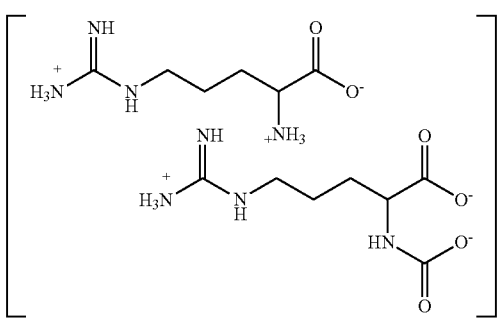

1.15 Complex 1 or any of 1.1 et seq. wherein the complex is in hydrate form (e.g., monohydrate or dihydrate or polyhydrate).

1.16 Complex 1.15, wherein the complex is in dihydrate form.

1.17 Complex 1 or any of 1.1 et seq. wherein the complex is substantially pure (e.g., greater than 80% pure, or greater than 85% pure, or greater than 90% pure, or greater than 95% pure).

1.18 Complex 1 or any of 1.1 et seq. wherein the complex is in solid form.

1.19 Complex 1 or any of 1.1 et seq. wherein the complex is in crystal form.

1.20 Complex 1 or any of 1.1 et seq. wherein the complex is in aqueous solution, e.g., solution consisting essentially of the complex and water.

1.21 Complex 1 or any of 1.1 et seq. wherein the complex is in aqueous solution consisting of at least 30 wt % complex, e.g., at least 40 wt % complex, or at least 50 wt % complex, or at least 60 wt % complex.

1.22 Complex 1 or any of 1.1 et seq. wherein the complex is in aqueous solution consisting of water and the complex, wherein the solution comprises at least 30 wt % amino acid, e.g., at least 40 wt % amino acid, or at least 50 wt % amino acid, or at least 60 wt % amino acid, or at least 70 wt % amino acid, optionally wherein the amino acid is arginine, lysine or glycine.

1.23 Complex 1 or any of 1.1 et seq. wherein complex is substantially free of free amino acid (e.g., amino acid that is not part of the complex, including amino acid in free base form or amino acid in salt form), e.g., wherein the complex has less than 10 wt % free amino acid, or less than 5 wt % free amino acid, or less than 3 wt % free amino acid, or less than 1 wt % free amino acid, optionally wherein the amino acid is arginine, lysine or glycine.

1.24 Complex 1 or any of 1.1 et seq. wherein the complex is prepared according to Method 1, or any of 1.1 et seq.

In a second aspect, the invention provides a method (Method 1) of making an amino acid carbamate complex of the formula $M^+$ [amino acid-carbamate]$^-$ which comprises an amino acid carbamate anion and a counterion M, wherein M is a metal cation or an amino acid cation (e.g., Complex 1 or any of 1.1 et seq.), comprising the steps of (1) dissolving or suspending an amino acid, in free base or salt form, and optionally a source of the cation M, in water, (2) adding carbon dioxide, in gaseous or solid form, (3) maintaining the pH of the solution above pH 8.0, optionally by adding an inorganic base, and (4) obtaining the resultant Complex. It is understood that where M is an amino acid which is the same amino acid as in the amino acid carbamate, then the reaction proceeds with a step (1) of dissolving or suspending an amino acid, in free base or salt form, in water, without the addition of an M source. Where M is not the same amino acid as used to form the carbamate, e.g., where M is a metal ion or an alternative amino acid, then the source of the cation M refers to either a basic salt of the metal M or a basic salt of the amino acid selected (e.g., the source of M may be, for example, sodium hydroxide, or sodium carbonate, or lysine carbonate or glycine hydrochloride).

In further embodiments of the second aspect, the invention provides:

1.1 Method 1, wherein the amino acid is in free base form (e.g., arginine free base).

1.2 Method 1, wherein the amino acid is in salt form (e.g., arginine hydrochloride).

1.3 Method 1 or any of 1.1 et seq., wherein the M source is a basic metal salt (e.g., a sodium salt, a potassium salt, or a lithium salt).

1.4 Method 1 or any of 1.1 et seq., wherein the M source is an amino acid in salt form (e.g., an amino acid addition salt, for example, a hydrochloride, or a carbonate, or a bicarbonate, or a sulfate, or a phosphate).

1.5 Method 1 or any of 1.1 et seq., wherein the M source is an amino acid which is the same as the amino acid of step (1).

1.6 Method 1 or any of 1.1 et seq., wherein the pH of the reaction is maintained at pH 8.5 or above, e.g. pH 9.0 or above, or pH 9.5 or above, or about pH 9.0.

1.7 Method 1 or any of 1.1 et seq., wherein an inorganic base is added to maintain the desired pH of the reaction.

1.8 Method 1.7, wherein the base is selected from an oxide, hydroxide, carbonate or bicarbonate of an alkali metal or alkaline earth metal.

1.9 Method 1.8, wherein the base is selected from sodium hydroxide, potassium hydroxide, lithium hydroxide, sodium bicarbonate, potassium bicarbonate, lithium bicarbonate, sodium carbonate, potassium carbonate, lithium carbonate, sodium oxide, potassium oxide, or lithium oxide.

1.10 Method 1.9, wherein the base is sodium hydroxide or sodium carbonate.

1.11 Method 1 or any of 1.1 et seq., wherein the base is added after the pH of the reaction mixture has dropped from its initial value to a value below pH 8.0.

1.12 Method 1 or any of 1.1 et seq., wherein the carbon dioxide is added as a gas, e.g., as a gas under pressure (e.g., at a pressure above 1 atmosphere, or above 1.5 atmospheres, or about 2 atmospheres, or above 3 atmospheres).

1.13 Method 1 or any of 1.1 et seq., wherein the carbon dioxide is added in solid form (i.e., as dry ice).

1.14 Method 1 or any of 1.1 et seq., wherein step (1) comprises adding amino acid free base to water to form a solution, suspension or slurry, optionally wherein the amino acid is arginine.

1.15 Method 1.14, wherein step (1) comprises adding amino acid free base to water to form a suspension or slurry, optionally wherein the amino acid is arginine.

1.16 Method 1 or any of 1.1 et seq., wherein the mixture of water and amino acid of step (1) is heated prior to the addition of carbon dioxide of step (2).

1.17 Method 1.16, wherein the mixture is heated to a temperature of at least 50° C., or at least 60° C., at least 70° C., or at least 80° C., e.g., from 50-90° C., or from 60-90° C., or from 70-90° C., or from 80-90° C., or about 70° C.

1.18 Method 1 or any of 1.1 et seq., wherein the temperature of steps (2) and (3) is maintained at at least 50°

C., or at least 60° C., at least 70° C., or at least 80° C., e.g., from 50-90° C., or from 60-90° C., or from 70-90° C., or from 80-90° C., or about 70° C.

1.19 Method 1 or any of 1.1 et seq., wherein step (4) comprises cooling the reaction mixture to room temperature (e.g., 20-30° C.), optionally, cooling the reaction mixture below room temperature (e.g. 0-20° C.).

1.20 Method 1 or any of 1.1 et seq., wherein the method provides Complex 1, or any of Complexes 1.1-1.24.

1.21 Method 1 or any of 1.1 et seq., wherein the method provides a concentrated solution of the Complex 1, or of any of Complexes 1.1-1.24, e.g., a solution having at least 40%, or at least 50%, or at least 60%, or at least 70%, or at least 80% by weight, of the Complex, e.g., about 80% or about 85% by weight of the Complex.

1.22 Method 1 or any of 1.1 et seq., wherein the method provides a concentrated solution of amino acid carbamate, for example arginine carbamate or lysine carbamate, e.g., a solution having at least 50%, or at least 60% or at least 70% or at least 80% by weight of the amino acid carbamate, e.g., about 80% or about 85% by weight.

The present Method 1, et seq., enables the preparation of concentrated solutions of the complex of the invention (i.e., Complex 1 or any of 1.1 et seq.). In some embodiments, Method 1, et seq., enables the preparation of concentrated solutions of amino acid carbamates (e.g., arginine carbamate). When carbon dioxide is bubbled into an aqueous solution, the dissolution of carbon dioxide to form aqueous carbonic acid results in a drop in the pH of the solution. When carbon dioxide is added to an aqueous solution of free base arginine (typical pH~10-11), it also results in a drop in pH as the arginine is consumed in the formation of arginine/arginine carbamate complex. However, as the pH drops below pH 9.0 (the second pKa of arginine), any un-reacted free base arginine becomes protonated, thus inhibiting further formation of arginine carbamate, and thus further formation of arginine/arginine carbamate complex. This effectively limits the yield of the carbamate formation to about 50 mol %. Without being bound by theory, it is believed that by adding an appropriate base to maintain the pH above pH 8, however, the formation of amino acid carbonate complex can be made to continue, resulting in substantial or complete consumption of free base amino acid and formation of a concentrated aqueous solution of amino acid carbamate complex (e.g., sodium amino acid carbamate complex).

Without being bound by theory, it is also known that primary aliphatic amines can reversibly form carbamates upon spontaneous reaction with carbon dioxide, but the equilibrium for these reaction favors the primary amine. Thus, carbamate formation from aliphatic amines with carbon dioxide is disfavored and it is not expected to spontaneously result in appreciable quantities of amine carbamate. Even under continuous provision of carbon dioxide, it becomes more likely that an inorganic carbonate salt will form, rather than a carbamate. However, without being bound by theory, it is believed that the formation of amino acid/amino acid carbamate complex (e.g., [arginine][arginine carbamate] complex) stabilizes the carbamate bond and inhibits the N-decarboxylation reaction from reverting the carbamate to free amine. Similarly, in the presence of an added metal ion inorganic base, the formation of a metal/amino acid carbamate complex (e.g., [Na][arginine carbamate] complex) stabilizes the carbamate against reversion to the free amino acid.

In a third aspect, the invention provides an oral care composition (Composition 1), comprising Complex 1 or any of Complexes 1.1-1.24;

e.g., 1.1. Composition 1, wherein the complex is present in an amount of 0.05 to 10% by weight of the composition, optionally at least 0.1, at least 0.2, at least 0.3, at least 0.4, at least 0.5, at least 1, at least 2, at least 3, or at least 4 up to 10% by weight of the composition, e.g. about 1-3%, e.g., about 2-2.7% by weight.

1.2. Composition 1 or 1.1, wherein the complex is present in an amount to provide amino acid in an amount of 0.05 to 30% by weight of the composition, optionally at least 0.1, at least 0.2, at least 0.3, at least 0.4, at least 0.5, at least 1, at least 2, at least 3, at least 4, at least 5, at least 10, at least 15, at least 20 up to 30% by weight, e.g., about 1-10% by weight.

1.3. Any of the foregoing compositions wherein the composition is an oral care composition, e.g., selected from a dentifrice, toothpaste, tooth powder, gel, or mouthwash.

1.4. Any of the foregoing compositions further comprising an effective amount of a fluoride ion source, e.g., providing 500 to 3000 ppm fluoride.

1.5. Any of the foregoing compositions further comprising an effective amount of fluoride, e.g., wherein the fluoride source is selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.6. Any of the preceding compositions comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these, e.g., in an amount of 1-20%, e.g., 2-8%, e.g., ca. 5%, by weight of the composition.

1.7. Any of the foregoing compositions comprising buffering agents, e.g., sodium phosphate buffer (e.g., sodium phosphate monobasic and disodium phosphate).

1.8. Any of the foregoing compositions comprising a humectant, e.g., selected from glycerin, sorbitol, propylene glycol, polyethylene glycol, xylitol, and mixtures thereof, e.g. comprising at least 20%, e.g., 20-40%, e.g., 25-35% glycerin.

1.9. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.10. Any of the preceding compositions further comprising a viscosity modifying amount of one or more of polysaccharide gums, for example xanthan gum or carrageenan, silica thickener, and combinations thereof.
1.11. Any of the preceding compositions further comprising flavoring, fragrance and/or coloring.
1.12. Any of the foregoing compositions further comprising an effective amount of one or more antibacterial agents, for example comprising an antibacterial agent selected from halogenated diphenyl ether (e.g. triclosan), herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
1.13. Any of the preceding compositions further comprising a whitening agent, e.g., a selected from the group consisting of peroxides, metal chlorites, perborates, percarbonates, peroxyacids, hypochlorites, and combinations thereof.
1.14. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.
1.15. Any of the preceding compositions further comprising a breath freshener, fragrance or flavoring.
1.16. Any of the foregoing compositions, wherein the pH of the composition is approximately neutral, e.g., from pH 6 to pH 9 e.g., 7 to 9, or 7 to 8, or 7 to 7.5 or 7.5 to 8, or about pH 7.5.
1.17. Any of the foregoing compositions, wherein the composition comprises water in an amount of less than 10% by weight, e.g., from 0.1 to 10%, or 0.1 to 5% or 0.1 to 3%, by weight of the composition.
1.18. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

In addition to the known benefits of oral care compositions which comprise basic amino acid such as arginine, it is believed that compositions which comprise basic amino acid (e.g. arginine) in the form of the amino acid carbamate complex of the present invention (Complex 1 or any of 1.1-1.24) to have improved compatibility with common toothpaste ingredients, especially the negatively charged polysaccharide gums, other anionic polymers (e.g., methyl vinyl ether/maleic anhydride or polyacrylate polymers) and anionic surfactants (e.g., sodium lauryl sulfate). This results in improved shelf stability and consumer acceptance.

The invention further provides a method of making a composition of the invention, e.g., any of Composition 1, et seq., comprising adding a complex of the invention, e.g., any of Complex 1, et seq., to a suitable oral care base composition, and further adding any additional oral care excipients or ingredients to produce an oral care composition. In some embodiments, the oral care base composition is a dentifrice or mouthwash base.

The invention further provides a method to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of an arginine/arginine carbamate complex, e.g., any of Complex 1, et seq., or a composition of the invention, e.g., any of Composition 1, et seq. to the teeth or oral cavity of a person in need thereof.

In various embodiments, the invention provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Complexes 1, et seq., or any of Compositions 1, et seq. as described above, to the oral cavity of a person in need thereof, e.g., one or more times per day. The invention further provides Complexes 1, et seq. and Compositions 1, et seq. for use in any of these methods.

In fourth aspect, the invention provides a method of making a concentrated solution of a basic amino acid carbamate (e.g., lysine carbamate or arginine carbamate) comprising the steps of (1) dissolving or suspending the amino acid, in free base or salt form, in water, (2) adding carbon dioxide, in gaseous or solid form, (3) maintaining the pH of the solution above pH 8.0, optionally by adding an inorganic base (Method 2). Further embodiments of the fourth aspect provide:
2.1 Method 2, wherein the amino acid is in free base form.
2.2 Method 2, wherein the amino acid is in salt form (e.g., arginine hydrochloride).
2.3 Method 2 or any of 2.1 et seq., wherein the amino acid is lysine, or wherein the amino acid is arginine.
2.4 Method 2 or any of 2.1 et seq., wherein the pH of the reaction is maintained at pH 8.5 or above, e.g. pH 9.0 or above, or pH 9.5 or above, or about pH 9.0.
2.5 Method 2 or any of 2.1 et seq., wherein an inorganic base is added to maintain the desired pH of the reaction.

2.6 Method 2.5, wherein the base is selected from an oxide, hydroxide, carbonate or bicarbonate of an alkali metal or alkaline earth metal.

2.7 Method 2.6, wherein the base is selected from sodium hydroxide, potassium hydroxide, lithium hydroxide, sodium bicarbonate, potassium bicarbonate, lithium bicarbonate, sodium carbonate, potassium carbonate, lithium carbonate, sodium oxide, potassium oxide, or lithium oxide.

2.8 Method 2.7, wherein the base is sodium hydroxide or sodium carbonate.

2.9 Method 2 or any of 2.1 et seq., wherein the base is added after the pH of the reaction mixture has dropped from its initial value to a value below pH 8.0.

2.10 Method 2 or any of 2.1 et seq., wherein the carbon dioxide is added as a gas, e.g., as a gas under pressure (e.g., at a pressure above 1 atmosphere, or above 1.5 atmospheres, or about 2 atmospheres, or above 3 atmospheres).

2.11 Method 2 or any of 2.1 et seq., wherein the carbon dioxide is added in solid form (e.g., as dry ice).

2.12 Method 2 or any of 2.1 et seq., wherein step (1) comprises adding the amino acid free base to water to form a solution, suspension or slurry.

2.13 Method 2.12, wherein step (1) comprises adding the amino acid free base to water to form a suspension or slurry.

2.14 Method 2 or any of 2.1 et seq., wherein the mixture of water and the amino acid of step (1) is heated prior to the addition of carbon dioxide of step (2).

2.15 Method 2.14, wherein the mixture is heated to a temperature of at least 50° C., or at least 60° C., at least 70° C., or at least 80° C., e.g., from 50-90° C., or from 60-90° C., or from 70-90° C., or from 80-90° C., or about 70° C.

2.16 Method 2 or any of 2.1 et seq., wherein the temperature of steps (2) and (3) is maintained at at least 50° C., or at least 60° C., at least 70° C., or at least 80° C., e.g., from 50-90° C., or from 60-90° C., or from 70-90° C., or from 80-90° C., or about 70° C.

2.17 Method 2 or any of 2.1 et seq., wherein step (4) comprises cooling the reaction mixture to room temperature (e.g., 20-30° C., optionally, cooling the reaction mixture below room temperature (e.g. 0-20° C.).

2.18 Method 2 or any of 2.1 et seq., wherein the method provides Complex 1, or any of Complexes 1.1-1.24.

2.19 Method 2 or any of 2.1 et seq., wherein the method provides a concentrated solution of amino acid carbamate, for example arginine carbamate or lysine carbamate, e.g., a solution having at least 50%, or at least 60% or at least 70% or at least 80% by weight of the amino acid carbamate.

Oral care compositions of the invention include any oral care formulation known in the art, for example a toothpaste, gel, mouthwash, powder, cream, strip, gum, or any other known in the art.

The benefits of the oral care compositions of the invention are numerous. By providing amino acid containing species, e.g., arginine and arginine derivatives, in the oral cavity, the oral care compositions of the invention provide antimicrobial, antiplaque, anti-gingivitis, anti-malodor, anti-caries, and/or anticalculus benefits. Basic amino acids, such as arginine, lead to higher pH of the plaque and can provide anti-caries benefits. In addition, basic amino acids, such as arginine, can enhance the activity of arginolytic bacteria, leading to a more-healthy plaque. Additional benefits include but are not limited to anti-attachment, anti-periodontitis and anti-bone loss, as well as promotion of wound healing.

In certain embodiments, the Compositions described herein, i.e., Compositions 1, et seq., comprise the complex (Complex 1 et seq.) in an amount of 0.05 to 10% by weight of the composition. In some embodiments, the amount of the complex can be varied for the desired purpose, such as a dentifrice or a mouthwash. In other embodiments, the amount of the complex is at least 0.1, at least 0.2, at least 0.3, at least 0.4, at least 0.5, at least 1, at least 2, at least 3, or at least 4 up to 10% by weight of the composition. In other embodiments, the amount of the complex is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In certain embodiments, the composition is anhydrous. By anhydrous, it is meant that there is less than 5% by weight water, optionally less than 4, less than 3, less than 2, less than 1, less than 0.5, or less than 0.1% water, down to 0%, by weight water.

The carrier represents all other materials in the composition other than the complex. The amount of carrier is then the amount necessary to reach 100% by adding to the weight of the complex.

Oral Care Active Agents:

The compositions of the invention may comprise various agents which are active to protect and enhance the strength and integrity of the enamel and tooth structure and/or to reduce bacteria and associated tooth decay and/or gum disease. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. For example, the composition may comprise arginine, when present, may be present at levels from, e.g., about 0.1 to about 20 wt % (expressed as weight of free base), e.g., about 1 to about 10 wt % for a consumer toothpaste or about 7 to about 20 wt % for a professional or prescription treatment product. Fluoride where present may be present at levels of, e.g., about 25 to about 25,000 ppm, for example about 750 to about 2,000 ppm for a consumer toothpaste, or about 2,000 to about 25,000 ppm for a professional or prescription treatment product. Levels of antibacterial agents will vary similarly, with levels used in toothpaste being e.g., about 5 to about 15 times greater than used in mouthrinse. For example, a triclosan toothpaste may contain about 0.3 wt % triclosan.

Fluoride Ion Source:

The oral care compositions may further include one or more fluoride ion sources, e.g., soluble fluoride salts.

A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat.

No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Abrasives:

The compositions of the invention, e.g., Composition 1 et seq. include silica abrasives, and may comprise additional abrasives, e.g., a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$), also sometimes referred to herein as (DiCal) or calcium pyrophosphate; calcium carbonate abrasive; or abrasives such as sodium metaphosphate, potassium metaphosphate, aluminum silicate, calcined alumina, bentonite or other siliceous materials, or combinations thereof.

Other silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

Foaming Agents:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of of foaming agent in the oral care composition (e.g., a single dose) is about 0.01 to about 0.9% by weight, about 0.05 to about 0.5% by weight, and in another embodiment about 0.1 to about 0.2% by weight.

Surfactants:

The compositions useful in the invention may contain anionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate ($CH_3(CH_2)_{10}CH_2(OCH_2CH_2)_2OSO_3Na$).

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar Control Agents:

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$), e.g., in amounts of about 3-4% of the sodium phosphate dibasic and about 0.2-1% of each of the pyrophosphates. In another embodiment, the compositions comprise a mixture of tetrasodium pyrophosphate (TSPP) and sodium tripolyphosphate (STPP)($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., about 5-15%, by weight of the composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight, e.g., about 0.5 to about 1.5% by weight.

Polymers:

The oral care compositions of the invention may also include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water-soluble alkali metal (e.g., potassium and sodium) or ammonium salts.

Silica thickeners, which form polymeric structures or gels in aqueous media, may be present. Note that these silica thickeners are physically and functionally distinct from the particulate silica abrasives also present in the compositions, as the silica thickeners are very finely divided and provide little or no abrasive action. Other thickening agents are carboxyvinyl polymers, carrageenan, hydroxyethyl cellulose and water-soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate can also be used as component of the thickening composition to further improve the composition's texture. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available, for example, as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In one embodiment of the invention, the principal humectant is glycerin, which may be present at levels of greater than 25%, e.g. 25-35% about 30%, with 5% or less of other humectants.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1: Synthesis of Arginine/Arginine Carbamate and Glycine/Glycine Carbamate Complexes De-ionized water, arginine or glycine free base, carbon dioxide and sodium hydroxide and/or sodium carbonate are combined as provided in Table 1 below. De-ionized water is first added to an empty reactor and heated up to 70° C. The amino acid is then added, and then carbon dioxide is bubbled through while maintaining the temperature at 65° C. Carbon dioxide addition is continued until a pH target is reached ("Target pH"). At that time, 50% aqueous sodium hydroxide solution, and/or solid sodium carbonate, is slowly added to raise the pH and maintain the pH at the target value while carbon dioxide addition is continued. When the final pH target is reached, the reaction solution is cooled to 40° C. and a sample is removed for nuclear magnetic resonance (NMR) analysis. As a negative control, the same procedure is followed without the addition of sodium hydroxide solution, and the pH of the reaction is allowed to proceed along its natural course. The NMR results are shown in Table 2 below.

TABLE 1

| Preparation | Water | Amino Acid | NaOH (50% Aq.) | $Na_2CO_3$ (solid) | Target pH | Final pH |
|---|---|---|---|---|---|---|
| 1A (Arg) | 200 g | 261 g | 91 g | | 8.9 | 9.0 |
| 1B (Arg) | 300 g | 261 g | 144 g | | 9.5 | 9.8 |
| 1C (Arg) | 200 g | 261 g | 210 g | | 9.5 | 10.2 |
| 1D (Arg) | 200 g | 261 g | 0 g | | — | <9 |
| 2A (Gly) | 303 g | 240 g | 60 g | 35 g | 7.8 | 8.3 |
| 2B (Gly) | 7.59 g | 1 g | | 1.41 g | | 9.8 |

TABLE 2

| Preparation | % Amino Acid Carbamate | % Amino Acid |
|---|---|---|
| 1A | 71.6 | 28.4 |
| 1B | 85.4 | 14.6 |
| 1C | 80.3 | 19.7 |
| 1D | 40.8 | 59.2 |
| 2A | 43.7 | 56.3 |
| 2B | 74.3 | 25.7 |

Carbamate formation is determined by proton NMR on a Bruker Advance spectrometer with a 5 mm BBI probe operating at 500 MHz (90° radiofrequency pulse with recycle delay of 10 seconds). Molar fractions of amino acid and amino acid carbamate are calculated based on peak integrals of the alpha-amino protons.

The results show that adding sodium hydroxide or sodium carbonate to maintain the pH of the reaction at 9.5 or above results in a conversion of amino acid to amino acid carbamate above 50 mol %, and even as much at 85 mol %. This is substantially higher than that obtained without added base (which results in a theoretical maximum conversion of about 50 mol %).

Example 2: Arginine/Arginine Carbamate Complex Structure

A single crystal of material believed to be arginine/arginine carbamate complex is analyzed by single-crystal X-ray diffraction to confirm its three-dimensional structure. The crystal is obtained by reacting arginine with carbon dioxide at a pH maintained at about pH 8.5, substantially as described in Example 1 (Preparation 1D). Powder x-ray diffraction (PXRD) is recorded on a Rigaku Ultima IV X-Ray diffractometer using Cu Kα radiation ($\lambda$=1.5406 Å). A graphite monochromator is used and the generator power setting is set to 40 kV and 44 mA. Data is collected between a 2θ angle of 3 to 50° with a step size of 0.02° and a scanning speed of 4.0 deg/min. The X-ray diffraction pattern confirms that the material is a complex consisting of one cationic arginine residue, one anionic arginine carbamate residue and two water molecules. The two amino acid residues align themselves substantially co-linearly. The data from Example 1 and Example 2 are both consistent with the structure of the complex of Preparation 1D as:

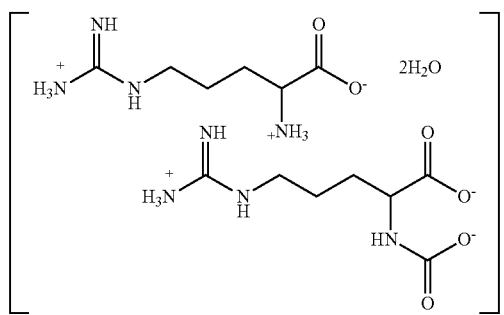

Example 3: Interaction of Arginine/Arginine Carbamate Complex with Calcium

Materials and Preparation Method—Part I: $CaCO_3$+Arginine Carbamate Complex

A total of 4 samples are prepared, three of which have an arginine species, and one of which is a negative control without arginine. The ratios of $CaCO_3$ to arginine, and pH of solutions are matched to a commercial sensitivity relief toothpaste (Table 1). The samples either comprise L-arginine free base (Sample 2), Preparation 1D (Sample 3), Preparation 1B (Sample 4), or no added arginine compound (Sample 1).

TABLE 1

Raw materials and their quantities used in preparation of samples 1, 2, 3, and 4.

| Reagent (g) | Sample 1 Replica I | Sample 1 Replica II | Sample 2 Replica I | Sample 2 Replica II | Sample 3 Replica I | Sample 3 Replica II | Sample 4 Replica I | Sample 4 Replica II |
|---|---|---|---|---|---|---|---|---|
| $CaCO_3$ | 12.5053 | 12.5037 | 12.5046 | 12.5026 | 12.5023 | 12.5059 | 12.5064 | 12.5026 |
| L-Arginine | — | — | 4.0025 | 4.0046 | — | — | — | — |
| Prep. 1D | — | — | — | — | 9.8030 | 9.8115 | — | — |
| Prep 1B | — | — | — | — | — | — | 11.7685 | 11.7660 |
| $H_2O$ | 34.3550 | 34.3436 | 34.3424 | 34.3433 | 28.5360 | 28.5500 | 26.5699 | 26.5700 |

Sample 1: $CaCO_3$ powder is combined with water followed by pH adjustment to pH=8.9. The mixture is stirred for about 4 hours and allowed to equilibrate for 4 days. The supernatant is isolated by centrifugation, filtered through 0.45 micron filter and submitted for calcium analysis. The sample is done in two replicas.

Sample 2: Arginine powder is dissolved in water and pH is adjusted to pH=8.9 with HCl. $CaCO_3$ powder is added to arginine solution and the resulting mixture is stirred for about 4 hours and allowed to equilibrate for 4 days. The supernatant is isolated by centrifugation, filtered through 0.45 micron filter and submitted for calcium analysis. The sample is done in two replicas.

Sample 3: Preparation 1D is combined with $CaCO_3$ and water, followed by pH adjustment with NaOH to pH=8.9. The mixture is stirred for about 4 hours and allowed to equilibrate for 4 days. The supernatant is isolated by centrifugation, filtered through 0.45 micron filter and submitted for calcium analysis. The sample was done in two replicas.

Sample 4: Preparation 1B is combined with water and pH is adjusted to pH=8.9 with HCl. $CaCO_3$ powder is added to the resulting solution and the mixture is stirred for about 4 hours and allowed to equilibrate for 4 days. The supernatant is isolated by centrifugation, filtered through 0.45 micron filter and submitted to calcium analysis. The sample is done in two replicas.

Materials and Preparation Method—Part II: $CaCl_2$+Arginine Carbamate Complex

A total of 3 samples are prepared in this study. Table 2 lists the amounts of each ingredient. The samples either comprise L-arginine free base (Sample 1), Preparation 1D (Sample 2), or Preparation 1B (Sample 3).

TABLE 2

Raw materials and their quantities used in preparation of samples 1, 2, 3.

| Reagent (g) | Sample 1 | | Sample 2 | | Sample 3 | |
|---|---|---|---|---|---|---|
| | Replica I | Replica II | Replica I | Replica II | Replica I | Replica II |
| $CaCl_2 \cdot 2H_2O$ | 2.0016 | 2.0011 | 2.0020 | 2.0011 | 2.0008 | 2.0014 |
| L-Arginine | 4.0034 | 4.0018 | — | — | — | — |
| Preparation 1D | — | — | 3.9991 | 4.0078 | — | — |
| Preparation 1B | — | — | — | — | 3.9999 | 4.0063 |
| $H_2O$ | 30.0036 | 30.0490 | 30.0213 | 30.0441 | 30.0066 | 30.0028 |

Sample 1: Arginine powder is dissolved in water followed by pH adjustment with HCl to pH=8. $CaCl_2$ powder is added to the arginine solution and stirred/vortex for 5 min until all $CaCl_2$ is dissolved. The resulting solution is clear with no obvious signs of precipitate formation. The sample is done in two replicas.

Sample 2: Preparation 1D is combined with water followed by pH adjustment with HCl to pH=8. $CaCl_2$ powder is added to the solution and stirred/vortex for 5 min. The resulting solution shows obvious signs of precipitate formation. The sample is done in two replicas.

Sample 3: Preparation 1B is combined with water followed by pH adjustment with HCl to pH=8. $CaCl_2$ powder is added to the solution and stirred/vortex for 5 min. The resulting solution shows obvious signs of precipitate formation. The sample is done in two replicas.

After the preparation, all the samples are left to equilibrate at room temperature for at least 1 day. The samples are then centrifuged and the supernatant is carefully removed. The supernatant is filtered through 0.2 micron filter and submitted for calcium and arginine analysis. The centrifuge tubes with precipitates are dried in the vacuum oven at 50° C. for 2 days. Sample 1 is used as a control, since no precipitate formation takes place. Once the tubes are dry, their masses are recorded and the tubes are placed back in the oven for 1 additional day. Tubes' weights are recorded again; no substantial change in mass is detected confirming that precipitates were dry.

Elemental Analysis:

Analysis for calcium (Ca) and arginine (Arg) is completed using ICP-OES and HPLC-UV methods, respectively.

Results—$CaCO_3$+Arginine Carbamate Complex—Part I:

Table 3 summarizes the results of soluble calcium analysis for the $CaCO_3$ solutions prepared at pH=8.9. Sample 1 contains no arginine and therefore, can be used as a control to establish the effect of arginine on solubility of $CaCO_3$.

TABLE 3

Summary of calcium analysis for samples 1, 2, 3 and 4 (average of two replicas). The numbers are reported as the amount of soluble calcium to the total mass of the solution.

| | Sample 1 | Sample 2 | Sample 3 | Sample 4 |
|---|---|---|---|---|
| Ca, ppm | 147 ± 3.95 | 191 ± 3.36 | 27.4 ± 3.53 | 3.75 ± 1.02 |

As can be seen from these data, the addition of pure arginine to $CaCO_3$ results in an increased solubility of calcium carbonate compared to the control. In contrast, addition of arginine carbamate complexes significantly reduces the concentration of soluble calcium in the solution. Comparison of samples 3 and 4 indicates that the higher the amount of carbamate, the lower the solubility of $CaCO_3$. Thus, Sample 3, containing Preparation ID (about 40 mol % arginine carbamate) results in more soluble calcium than Sample 4, containing Preparation 1B (about 85 mol % arginine carbamate).

Results—$CaCl_2$+Arginine Carbamate Complex—Part II:

In this part of the study, the $CaCO_3$ compound is replaced with the soluble $CaCl_2$ salt to study the effect of calcium interaction with arginine carbamate solutions. The combination of $CaCl_2$ with arginine resulted in a formation of a clear solution with no obvious signs of precipitation. In contrast, combination of calcium chloride with arginine carbamate complexes leads to immediate formation of precipitate.

The supernatant is carefully removed and the tubes are dried at 50° C. in vacuum oven. The masses of the precipitates are presented in Table 4 along with the analytical results on the supernatant analysis. Sample 1 is used as a control.

TABLE 4

The masses of the precipitates and the results of soluble calcium and arginine analyses for the $CaCl_2$ solutions. Data are averages of two replicas. The numbers are reported as the amount of soluble calcium and/or arginine to the total mass of the solution.

| | Mass of precipitate, g | Ca, % | | Arginine, % | |
|---|---|---|---|---|---|
| | | Calculated | Experimental | Calculated | Experimental |
| Sample 1 | 0.016 ± 0.013 | 1.43 | 1.36 ± 0.063 | 10.5 | 10.5 ± 0.14 |
| Sample 2 | 0.368 ± 0.005 | 1.51 | 1.16 ± 0.042 | 4.51 | 4.6 ± 0.071 |
| Sample 3 | 0.521 ± 0.014 | 1.49 | 0.838 ± 0.014 | 3.71 | 3.8 ± 0.068 |

The experimental findings from the $CaCl_2$ solutions are in agreement with the studies on $CaCO_3$ (part I). In presence of pure arginine there is no precipitate formation and practically no loss of calcium (<5%) and/or arginine in the solution. With addition of arginine carbamate species ~23% and ~44% of calcium is lost due to the precipitate formation for samples 2 and 3, respectively. Note, that samples 2 and 3 have excess of calcium relative to arginine, so arginine carbamate is the limiting reagent in this study. The results from sample 3 demonstrate that higher arginine carbamate content results in more calcium precipitation. Finally, arginine data in the supernatant indicate no significant arginine loss, suggesting that the precipitate is the result of $CaCO_3$ formation when arginine carbamate interacts with calcium ions.

To summarize, the study of $CaCO_3$ and $CaCl_2$ interaction with arginine carbamate complex demonstrates that presence of carbamate species leads to calcium precipitation in the form of the calcium carbonate and to a significant reduction of the soluble calcium content in the solution. These results show that arginine carbamate complexes according to the invention can thus be used in applications where an in-situ $CaCO_3$ generation is preferable and/or where soluble calcium content needs to be reduced, for instance in tartar control applications.

Example 3: Toothpaste Composition Comprising Arginine/Arginine Carbamate Complex A toothpaste composition comprising 1B from Example 1 is prepared according to the formula shown in Table 1.

TABLE 5

| Ingredients | Wt % |
| --- | --- |
| Sodium carboxymethyl cellulose | 0-5 (e.g. 0.65) |
| Polyethylene glycol | 0-10 (e.g. 3) |
| Sorbitol, 70% Aq. Soln. | 20-80 (e.g. 50) |
| Distilled water | Q.S. |
| Sodium Fluoride | 0-5 (e.g. 0.24) |
| High Cleaning Silica | 0-20 (e.g. 10) |
| Abrasive Silica | 0-20 (e.g. 10) |
| Thickening Silica | 2.75 |
| Sodium Lauryl Sulfate | 1.5 |
| Cocamidopropylbetaine | 1.25 |
| Flavors/Colors/Sweeteners | 1.50 |
| Arginine Carbamate Complex (e.g., Preparation 1B) | 0.1-20% (e.g. 5) |
| Total | 100 |

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. An oral care composition comprising an amino acid carbamate complex of the formula $M^+$ [amino acid-carbamate]$^-$ which comprises an amino acid carbamate anion and a counterion M, wherein M is a metal cation or an amino acid cation, and wherein the composition is selected from a dentifrice, toothpaste, tooth powder, tooth gel, or mouthwash, and wherein the complex is present in an amount of 0.05 to 10% by weight of the composition.

2. The composition of claim 1, wherein M is the amino acid cation.

3. The composition of claim 1, wherein M is the amino acid cation wherein the amino acid is selected from the group consisting of glycine, arginine, lysine, histidine, alanine, valine, leucine, isoleucine, phenylalanine, tryptophan, glutamic acid, aspartic acid, glutamine, asparagine, serine, threonine, cysteine, methionine, proline, and tyrosine.

4. The composition of claim 1, wherein the amino acid carbamate is a carbamate of an amino acid selected from the group consisting of glycine, arginine, lysine, histidine, alanine, valine, leucine, isoleucine, phenylalanine, tryptophan, glutamic acid, aspartic acid, glutamine, asparagine, serine, threonine, cysteine, methionine, proline, and tyrosine.

5. The composition of claim 1, wherein the complex has the formula [glycine]$^+$[glycine carbamate]$^-$, [lysine]$^+$[lysine carbamate]$^-$, [arginine]$^+$[arginine carbamate]$^-$, $Na^+$[arginine carbamate]$^-$, $Na^+$[lysine carbamate]$^-$ or $Na^+$[glycine carbamate]$^-$.

6. The composition of claim 1, wherein the composition comprises an effective amount of a fluoride ion source.

7. The composition of claim 1, wherein the composition comprises an abrasive.

8. The composition of claim 1, wherein the composition comprises a surfactant.

9. A method of making the amino acid carbamate complex of claim 1, comprising the steps of (1) dissolving or suspending an amino acid, in free base or salt form, and a source of the cation M, in water to form a mixture, (2) adding to the mixture a carbon dioxide, in gaseous or solid form, (3) maintaining the pH of the solution above pH 8.0, optionally by adding an inorganic base, and (4) obtaining the resultant complex.

10. The method of claim 9, wherein the amino acid is arginine in free base form.

11. The method of claim 9, wherein the pH of the solution is maintained at pH 8.5 or above.

12. The method of claim 9, wherein the inorganic base is added to maintain the pH of the solution, optionally wherein the base is selected from an oxide, hydroxide, carbonate or bicarbonate of an alkali metal or alkaline earth metal.

13. The method of claim 12, wherein the base is selected from sodium hydroxide, potassium hydroxide, lithium hydroxide, sodium bicarbonate, potassium bicarbonate, lithium bicarbonate, sodium carbonate, potassium carbonate, lithium carbonate, sodium oxide, potassium oxide, or lithium oxide.

14. The method of claim 9, wherein the mixture of water, source of the cation M, and amino acid of step (1) is heated prior to the addition of carbon dioxide of step (2).

15. The method of claim 14, wherein the mixture is heated to a temperature of at least 50° C., or at least 60° C., at least 70° C., or at least 80° C.

16. A method of making the oral care composition of claim 1, comprising adding an arginine/arginine carbamate complex obtained by the method according to claim 9 to a oral care base composition, and further adding additional oral care excipients or ingredients to produce an oral care composition.

17. A method to reduce acid erosion of the enamel, clean the teeth, reduce bacterially-generated biofilm and plaque, reduce gingivitis, inhibit tooth decay and formation of cavities, and reduce dentinal hypersensitivity, comprising applying the composition according to claim 1 to the teeth or oral cavity of a person in need thereof.

18. The method of claim 9, wherein the pH of the solution is maintained at pH 9.0 or above, pH 9.5 or above, or about pH 9.0.

19. The method of claim 14, wherein the mixture is heated to a temperature of from 50-90° C., from 60-90° C., from 70-90° C., from 80-90° C., or about 70° C.

* * * * *

UNITED STATES PATENT AND TRADEMARK OFFICE
CERTIFICATE OF CORRECTION

PATENT NO. : 10,857,083 B2
APPLICATION NO. : 16/216533
DATED : December 8, 2020
INVENTOR(S) : Long Pan et al.

Page 1 of 1

It is certified that error appears in the above-identified patent and that said Letters Patent is hereby corrected as shown below:

On the Title Page

Under "OTHER PUBLICATIONS", Lines 1-5,
delete "https://www.pronamel.us/tooth-erosion/how-to-prevent-acid-erosion/?gclid=-CjwKCAiA27LvBRBOEiwAPc8XWQuAVBzhTB9ih9LpZUYwsJgULsBhfA8FlgPb5vgaEX910HBwxP-NTrRoCwFMQAvD_BwE&gclsrc=aw.ds" and insert
-- https://www.pronamel.us/tooth-erosion/how-to-prevent-acid-erosion/?gclid=-CjwKCAiA27LvBRB0EiwAPc8XWQuAVBzhTB9ih9LpZUYwsJqULsBhfA8FlgPb5vgaEX9IOHBwxP-NTrRoCwFMQAvD_BwE&gclsrc=aw.ds --, therefor.

In the Specification

In Column 17, Line 49, delete "ofabout" and insert -- of about --, therefor.

In Column 24, Line 31, delete "ID" and insert -- 1D --, therefor.

Signed and Sealed this
Second Day of March, 2021

Drew Hirshfeld
*Performing the Functions and Duties of the
Under Secretary of Commerce for Intellectual Property and
Director of the United States Patent and Trademark Office*